(12) United States Patent
Sirimanne et al.

(10) Patent No.: US 6,761,700 B2
(45) Date of Patent: Jul. 13, 2004

(54) EXTRA-CORPOREAL VASCULAR CONDUIT

(75) Inventors: Laksen Sirimanne, Tustin, CA (US); Anthony Viole, Foothill Ranch, CA (US)

(73) Assignee: Orqis Medical Corporation, Lake Forest, CA (US)

(*) Notice: Subject to any disclaimer, the term of this patent is extended or adjusted under 35 U.S.C. 154(b) by 0 days.

(21) Appl. No.: 09/780,083

(22) Filed: Feb. 9, 2001

(65) Prior Publication Data

US 2002/0111577 A1 Aug. 15, 2002

(51) Int. Cl.$^7$ .............................................. A61M 37/00
(52) U.S. Cl. .................... 604/4.01; 604/6.16; 623/1.36; 623/3.26
(58) Field of Search .............................. 604/4.01, 5.01, 604/6.16, 7, 8, 48, 500, 104, 105, 106, 174, 264, 523, 524; 210/645, 646; 422/44–48; 623/1, 11, 12, 1.1, 1.13, 1.14, 1.24

(56) References Cited

U.S. PATENT DOCUMENTS

| | | | |
|---|---|---|---|
| 4,834,746 A | | 5/1989 | Kira |
| 4,925,452 A | * | 5/1990 | Melinyshyn et al. ....... 604/284 |
| 5,037,377 A | | 8/1991 | Alonso |

(List continued on next page.)

FOREIGN PATENT DOCUMENTS

| WO | WO 98/34676 | 8/1998 |
|---|---|---|
| WO | WO 99/19010 | 4/1999 |
| WO | WO 00/61207 | 10/2000 |
| WO | WO 00/76577 A1 | 12/2000 |
| WO | WO 00/76577 | 12/2000 |

OTHER PUBLICATIONS

International Search Report dated May 4, 2002; PCT/US 01/29542; filed Sep. 20, 2001.

*Primary Examiner*—Henry Bennett
*Assistant Examiner*—Nihir Patel
(74) *Attorney, Agent, or Firm*—Knobbe, Martens, Olson & Bear LLP (57) ABSTRACT

An extracorporeal vascular conduit for circulating blood outside a patient's body over an extended period of time in a manner that minimizes risk of thrombosis and complement activation and maximizes the ability of a patient to be ambulatory during recovery stages. The inventive vascular conduit comprises a first biocompatible material and a second synthetic material that is employed over a portion of the biocompatible material that extends outside the patient's body when is use. The majority of the portion that extends within the patient's body remains uncoated. A third synthetic material is applied around the conduit near the distal end of the second coating material of the catheter to permit a physician to secure the catheter to the patient's skin to minimize relative movement.

14 Claims, 4 Drawing Sheets

U.S. PATENT DOCUMENTS

| | | | | |
|---|---|---|---|---|
| 5,041,098 A | * | 8/1991 | Loiterman et al. | 604/175 |
| 5,152,782 A | | 10/1992 | Kowligi et al. | |
| 5,306,240 A | * | 4/1994 | Berry | 604/51 |
| 5,367,110 A | | 11/1994 | Tu et al. | |
| 5,411,550 A | | 5/1995 | Herweck et al. | |
| 5,453,084 A | * | 9/1995 | Moses | 604/8 |
| 5,584,876 A | | 12/1996 | Bruchman et al. | |
| 5,718,973 A | | 2/1998 | Lewis et al. | |
| 5,782,789 A | | 7/1998 | Herweck et al. | |
| 5,801,063 A | * | 9/1998 | Grandies et al. | 436/518 |
| 5,814,021 A | * | 9/1998 | Balbierz | 604/174 |
| 5,855,210 A | * | 1/1999 | Sterman et al. | 128/898 |
| 5,893,886 A | | 4/1999 | Zegdi et al. | |
| 5,902,336 A | * | 5/1999 | Mishkin | 623/11 |
| 5,968,089 A | | 10/1999 | Krajicek | |
| 5,976,192 A | | 11/1999 | McIntyre et al. | |
| 5,989,287 A | | 11/1999 | Yang et al. | |
| 5,997,496 A | * | 12/1999 | Sekiguchi et al. | 604/4 |
| 6,086,553 A | | 7/2000 | Akbik | |
| 6,102,884 A | * | 8/2000 | Squitieri | 604/8 |
| 6,135,981 A | * | 10/2000 | Dyke | 604/96.01 |
| 6,180,059 B1 | * | 1/2001 | Divino, Jr. et al. | 422/45 |
| 6,200,260 B1 | | 3/2001 | Bolling | |
| 6,299,575 B1 | | 10/2001 | Bolling | |
| 6,387,037 B1 | | 5/2002 | Bolling et al. | |
| 6,390,969 B1 | | 5/2002 | Bolling et al. | |
| 6,402,767 B1 | * | 6/2002 | Nash et al. | 606/153 |
| 6,428,464 B1 | | 8/2002 | Bolling | |
| 6,540,658 B1 | * | 4/2003 | Fasciano et al. | 600/17 |
| 6,558,356 B2 | | 5/2003 | Barbut | |
| 6,610,004 B2 | | 8/2003 | Viole et al. | |
| 6,685,621 B2 | | 2/2004 | Bolling et al. | |
| 2002/0169413 A1 | | 11/2002 | Keren et al. | |
| 2002/0188166 A1 | | 12/2002 | Viole et al. | |
| 2002/0188167 A1 | | 12/2002 | Viole et al. | |
| 2003/0069468 A1 | | 4/2003 | Bolling et al. | |
| 2003/0083617 A1 | | 5/2003 | St. Germain | |

\* cited by examiner

EXTRA-CORPOREAL VASCULAR CONDUIT

BACKGROUND OF THE INVENTION

1. Field of the Invention

The present invention relates to an artificial vessel and, in particular, to an apparatus and method for permitting long-term extracorporeal circulation of blood flow from and to the vasculature of a patient.

2. Description of the Related Art

It is often necessary to divert the flow of blood from a patient's blood vessel back to the same or a different blood vessel as part of treating a patient suffering from one or more of numerous health impairments, including cardiovascular ills. In many cases, such efforts involve using artificial means for carrying the blood between vessels. The materials selected for doing so depend often on whether the application is acute (short-term) or chronic (long-term). In either case, it is beneficial to employ biocompatible materials, although the extent of biocompatibility differs depending upon the duration of intended or expected use with the patient. Biocompatibility is generally measured by how little the synthetic material adversely affects the patient's blood and tissues. Materials that eventually destroy red blood cells or body tissues are generally not suitable particularly for long-term applications.

For short-term or acute applications, a wide range of polymer materials are available, such as polyethylene, silicone and polyvinyl chloride (PVC). While the level of biocompatibility for such polymer materials is not particularly high, for short-term use, the adverse effects on the patient tend to be minimal. For chronic or long-term applications of artificial blood vessels used for the diversion of blood, the need for a higher level of biocompatibility rises dramatically. Indeed, an entire industry has evolved around the development of biocompatible materials that may be formed as conduits to function as artificial vessels for carrying diverted blood to and from a patient's vascular system on a long-term basis. Examples of such materials are ePTFE (expanded polytetrafluroethylene) such as that manufactured by Bard Impra and woven polyester such as that manufactured by W. L. Gore. Discussions of such synthetic biocompatible materials may be found in U.S. Pat. Nos. 5,718,973, 5,629,008 and 5,549,657.

In many cases, the blood being diverted remains entirely within the patient's body; i.e., intracorporeal application, using a graft. Under those circumstances, the material chosen for long-term, purely internal, application need only withstand the conditions of a singular environment—the interior of the patient. In some cases, a portion of the patient's existing vascular system is used to divert the blood, ensuring complete biocompatibility. In other cases, synthetic materials are used for the graft, such as ePTFE or woven polyester. In one method of application, both ends of the artificial vessel are grafted directly to the patient's blood vessels. Where the artificial vessel is applied entirely within the patient's thorax, the vessel is often applied during open-chest surgery. In some cases, the artificial vessel is applied to blood vessels in a manner that does not require open-chest surgery. In those cases, the graft may be tunneled under the skin and surgically applied at both ends to the respective blood vessels. While common graft materials such as ePTFE and woven polyester are somewhat porous, it is not a problem as the pores in the wall of the graft eventually clot off.

Where there is a desire or need to divert the flow of blood externally to the patient for some period of time during treatment, the material selected to carry the blood should be capable of withstanding the conditions of two environments, that inside the body and that outside the body. Presently, the short-term application of diverting blood extracorporeally, such as perisurgical environments where the blood is diverted through an oxygenator outside the body, e.g., during cardiac surgery, an artificial vessel made of PVC is used to carry the blood. The connection to the patient's vascular system is typically made, under such circumstances, with cannulas temporarily inserted into the vasculature of the patient for both the inflow and the outflow. An example of such an artificial vessel is made by Medtronic, Inc. The nature of the PVC material is such that it is not porous, so there is no risk of blood seeping through the walls of the artificial vessel or contaminants passing to the blood from the external environment.

The long-term application of diverting blood extracorporeally involves the use of a bi-material conduit, where one portion of the conduit is made of a biocompatible material, such as ePTFE, and the other portion of the catheter is made of a polymer material such as PVC. Typically, the ePTFE portion is anastamosed to the patient's vasculature to permit fluid communication. The polymer portion of the catheter is used to connect to a pump and/or other device through which the blood passes.

There is one artificial vessel system manufactured by MEDOS AG, Germany that includes a closed end at the proximal end of the catheter, in which a small orthogonally positioned hole is provided to permit the physician to grasp the closed end with a hook. A tunneling guide is used to create a tunnel below the patient's skin through which the cannula may reside. The guide is then used to grasp the closed end of the vascular conduit and pull the proximal end of the vascular conduit through the tunnel created by the guide. A hemostat is placed over the proximal end of the conduit to seal the inner lumen and the closed end is then sliced off, permitting the proximal end of the cannula to be connected to a pump or other device. The hemostat can then be released to permit blood flow to the pump or the other device. This system provides a means for attaching the vascular conduit to the patient at a location different than the location where the vascular conduit exits the body. Where it is desired to locate the exit site proximate the connection site, no tunneling may be necessary.

Typical graft materials such as ePTFE and woven polyester are effective at diverting blood flow without adversely affecting the properties of the blood or the characteristics of the flow. However, as alluded to above, common graft materials are porous and are not successful in applications outside the body because of fluid communication with the ambient environment. Materials such as ePTFE and woven polyester, however, are simply not capable of withstanding extracorporeal environments without adversely affecting blood flow characteristics or without contamination of the blood. Contact of the blood with air may lead to contamination and infection or may lead to the more serious event of introducing air emboli into the blood stream. Thus, the industry presently relies upon the non-porous polymer materials to carry the blood outside the body. While easy to use, the problem with such materials is that they eventually have an adverse effect on the blood during prolonged use. Moreover, such materials eventually lead to poor sustained blood flow due to resulting thrombosis within the artificial vessel. Should the thrombus break away, it could lead to blood clots in other parts of the circuit or in the patient, the well known adverse results of which include occlusion of blood vessels potentially leading to stroke or myocardial infarction. In some cases, when using such polymer materials, a heparin coating has been applied to the polymer graft to minimize thrombosis. The long-term effectiveness of such an application is not certain.

SUMMARY OF THE INVENTION

Overcoming many if not all of the limitations of the prior art, the present invention comprises an extracorporeal vascular conduit for circulating blood outside a patient's body over an extended period of time in a manner that minimizes risk of thrombosis and inflammatory response and maximizes the ability of a patient to be ambulatory during recovery stages. The inventive vascular conduit solves the needs described above by employing a single lumen vascular conduit comprising a first biocompatible material that preferably extends the majority of the length of the cannula and a second material that surrounds the portion of the conduit that extends from outside the patient's body to just within the patient's body. The majority of the portion of the first material that extends within the patient's body does not have the second material. A third interface material is applied close to the distal end of the second material of the cannula to permit a physician to more effectively secure the catheter to the patient's skin to minimize relative movement. Such a unique arrangement provides for combining the advantage of having the blood come into contact solely with a proven biocompatible material with the advantage of using polymer materials that deal with the external environment more effectively and the advantage of immobilizing the cannula more effectively to the patient.

In one preferred embodiment, the present invention comprises an extracorporeal vascular conduit comprising a length of material, such as PTFE, which could particularly be ePTFE if so desired, having a first diameter, in which a portion of the ePTFE material proximal of the distal end is enshrouded with a thin coating of medical grade silicone or polyurethane. The distal end of the vascular conduit is configured to connect to a patient's vascular system via, for example, an end-to-side anastomosis connection. A polyester sleeve is provided close to the distal end of the thin coating of medical grade silicone or polyurethane, positioned to correspond with the skin exit site of the patient. At the proximal end, the catheter includes a relatively short, tapered section comprising silicone or polyurethane material for connecting to a pump or other device. The length of the conduit not covered by the second material depends upon where the treating physician desires to locate the transdermal site relative to the location of the connection to the patient's vascular system. In addition, a reinforcing member, such as a helical coil, may be provided for at least some of the length of the cannula.

In another embodiment, the distal end of the vascular conduit comprises a plurality of discrete smaller conduits each of which may be connected to the patient's vascular system at different locations. By providing a plurality of vascular connections, a large volume of flow within the vascular conduit in fluid communication with the patient may be achieved while the size of the individual conduits engaging blood vessels is maintained relatively small. This solves, among other things, sealing problems that arise as the diameter of the vascular conduit approaches the diameter of the vessel to which it attaches. Preferably, the multiple connection conduits converge distal to the transdermal penetration site so that blood flows out of the body in one conduit. As mentioned above, the plurality of discrete conduits may be made of ePTFE.

In yet another embodiment, the vascular conduit comprises a plurality of lumens. One of the lumens may be attached to a blood vessel, for example an artery of the patient's vascular system, while another lumen is attached to another blood vessel, for example, a vein of the patient's vascular system or another artery. Blood may be withdrawn from one vessel and then returned to the other. For example, blood in one of the patient's veins may be withdrawn and then recirculated to one of the patient's arteries. Alternatively, blood may be withdrawn from one of the patient's arteries and recirculated to one of the patient's veins. Of course, this conduit can also be used to withdraw blood from one of the patient's arteries and return it to a second artery; or blood may be withdrawn from one of the patient's veins and returned to another vein.

The above described embodiments, as well as other embodiments disclosed herein, could also employ various additional coatings. For example, an anti-bacterial or antimicrobial coating may be applied to reduce infection risk; an anti-thrombotic coating may be applied to reduce adhesions to the catheter housing and any other component that comes into contact with blood for any significant period of time.

In a preferred method of use, the present invention comprises the steps of (a) providing an extracorporeal vascular conduit comprising a first synthetic biocompatible material that extends substantially the length of the conduit, a second synthetic polymer material employed over the portion of the conduit configured to extend outside the patient's body to just within the patient's body, and a third interface material to enhance securement of the conduit to the patient's skin at the transdermal location, (b) securing a distal end of the extracorporeal vascular conduit to the patient's vascular system, and (c) connecting a proximal end of the extracorporeal vascular conduit to a pump, monitor, or other device used in and/or during the treatment of a patient. The method may further comprise the step of providing an anti-bacterial or anti-microbial coating to lessen infection risk.

BRIEF DESCRIPTION OF THE INVENTION

DETAILED DESCRIPTION OF THE INVENTION

Figure 1:
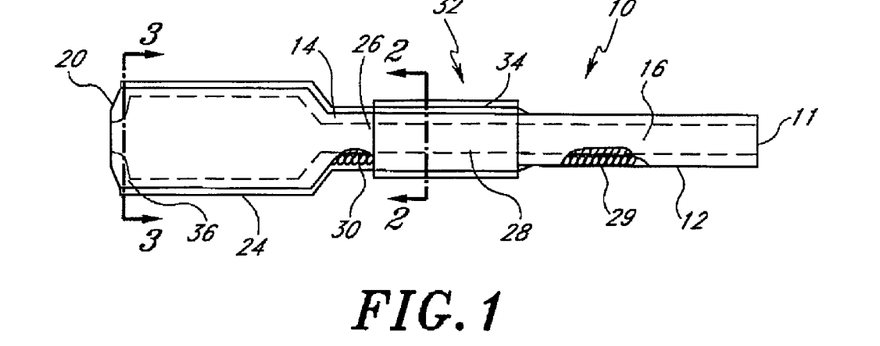
FIG. 1 is a side view of one embodiment of the present invention.
Figure 2:
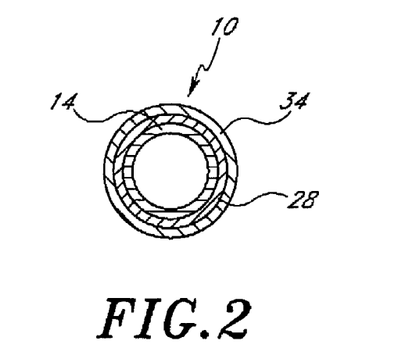
FIG. 2 is a longitudinal cross-sectional view of the embodiment of FIG. 1 taken along section 2—2.

Reference is now made to the figures wherein like parts are designated with like numerals throughout. In this document, "distal" refers to the direction of the end of the conduit designed for connection to the patient. "Proximal" refers to the direction of the end of the conduit behind to extend outside the patient's body. Referring to FIGS. 1 and 2, the present invention comprises an extracorporeal vascular conduit 10. The extracorporeal vascular conduit 10 comprises a first portion 12 and a second portion 14 that, together, comprise a substantial portion of the conduit 10. Both the first and second portion 12, 14 comprise a first synthetic biocompatible material 16, such as PTFE, including expanded PTFE (ePTFE), or woven polyester, or some other biocompatible material exhibiting similar characteristics and qualities. The first portion 12 corresponds to the portion of the conduit 10 that is configured to reside inside of the patient when the conduit 10 is applied to the patient. The second portion 14 corresponds to the portion of the conduit 10 that is configured to reside outside of the patient when the conduit 10 is applied to the patient. The conduit 10 has a distal end 18 comprising the distal end of the first portion 12 that is configured to be secured to a patient's vascular system. With such a configuration, the distal end 18 of the conduit 10 may be secured to a blood vessel via, for example, an end-to-side anastomosis connection. If desired, the biocompatible material 16 of the first and second portions may have a reinforcing configuration, employing either a discrete reinforcing member or, preferably, a helical reinforcement that traverses the length of the graft that comprises the biocompatible material, sometimes referred to as beading.

The conduit 10 also has a proximal end 20 that is configured to connect to a medical device (not shown) usable in the treatment of a patient, including but not limited to a pump, a vent, a sample site, a flow meter, or an oxygenator. In the preferred embodiment, the proximal end 20 of the conduit 10 comprises a third portion 24 that, if desired, may comprise a tapered section with its diameter larger from the distal to the proximal. The tapered section permits accommodation of a medical device having a diameter greater than the diameter of the conduit 10 at the first and second portions 12, 14. If desired, the present catheter may include a tapered section that has a smaller diameter from the distal to the proximal to accommodate a medical device having a diameter lesser than the diameter of the first and second portions of the catheter. Of course, no taper may be necessary, depending upon the size of the connection of the medical device. In a preferred embodiment, the inner diameter of the first and second portions 12, 14 is 6.0 mm and the outer diameter is 7.2 mm. Also, the inner diameter of the proximal end of the third portion 24 is 0.375 (⅜) inches to permit connection to medical devices having standard sized fittings.

Still referring to FIGS. 1 and 2, the present conduit 10 further comprises a second synthetic material 26 that surrounds the biocompatible material substantially along the length of the second portion 14 to form a second wall layer 28 of the conduit 10. In the preferred embodiment, the second synthetic material is silicone or urethane, although other materials having similar characteristics such as durability, resiliency, and imperviousness would be acceptable, including other polymers and rubbers. Like the first synthetic biocompatible material, the second synthetic material should be sufficiently resilient to bend easily so as to avoid significant discomfort to a patient during use. That is particularly important where it is desired that the patient be ambulatory when the extracorporeal vascular conduit is secured to the patient.

The second synthetic material 26 functions to overcoat the first synthetic biocompatible material 16 to form the second wall layer 28 (or overcoat) to prevent exposure of the biocompatible material 16 to the ambient environment. With such an arrangement, the vascular conduit 10 may be used extracorporeally for extended periods of time without significantly adversely affecting the patient's blood or its characteristics. The biocompatible material 16 minimizes risk of thrombosis and inflammatory response while the second synthetic material prevents seepage of the blood through the graft conduit walls and minimizes, thereby, risk of infection or the risk of air emboli. Preferably, the distal end of the second synthetic material 26 is located distal to the transdermal penetration site when the conduit 10 is applied to the patient. In other words, the point on the conduit 10 that protrudes through the skin of the patient should be proximal to the distal end of the second synthetic material 26, although alignment of the second synthetic material 26 and the transdermal penetration site would be acceptable while still preserving the functional advantages of the present invention. The length of the non-coated first portion depends upon where the treating physician desires to locate the exit site relative to the location of the connection to the patient's vascular system. For example, where the exit site of the patient is close to the vessel connection site, the length of non-coated portion would be relatively short.

The second synthetic material 26 may be applied in one of multiple acceptable manufacturing techniques, including dipping the first biocompatible material into a source of second synthetic material that hardens and cures securely around the first biocompatible material after removal from the source. Another acceptable technique would be preforming a sleeve of second synthetic material having an appropriate inner diameter that is slipped over the first biocompatible material and positioned at a desired location for welding or bonding in place. An injection molding technique may also be acceptable. Other techniques may be acceptable that effectively secure the second synthetic material at a fixed location around at least a portion of the first synthetic biocompatible material to prevent seepage of the interior fluid contents of the catheter to the ambient and to prevent exposure of the same to air-borne contaminants.

Preferably, the third portion 24 of the conduit 10, including any tapered section, is made from the second synthetic material, such as silicone, PVC or polyurethane, or other material exhibiting similar qualities and characteristics. Where the material selected for the overcoat 30 and the material selected for the third portion are the same, they may be made integral to each other in an acceptable manufacturing technique, such as those identified above. If not of the same material, or even if of the same material, the overcoat 28 of the second portion 14 and the third portion 24 may be made discretely and connected together using a mechanical connection or bonding. In either case, it is desired that the transition be as smooth as possible to avoid disrupting fluid flow and to avoid locations for potential thrombosis. Preferably, regardless of the manufacturing technique selected, the inner diameter of the second portion 14 of the conduit 10 is flush with the inner diameter of the third portion 24 so that the fluid sees no discontinuity in the wall surface, even where a taper is provided. That requires that the inner diameter of the distal end of the third portion 24 be the same as the inner diameter of the proximal end of the second portion 14. With the preferred embodiment, the proximal end of the biocompatible material (i.e., the proximal end of the second portion 14), therefore, abuts against the distal end of the third portion 24. In addition, gradual transitions are preferred from the inner diameter of the second portion 14 to the inner diameter of the third portion 24. Such gradual transitions may prevent undesirable turbulent flow.

Still referring to FIG. 1, a preferred embodiment of the conduit further comprises axial reinforcing member 30 preferably extending through all or a part of the conduit 10 to addstiffness to the conduit 10. The reinforcing member 30 may be a helical coil, as is known in the art. It need not be limited to helical coils, however, as other reinforcement means may be used. The axial reinforcing member 30 may not be necessary so long as the conduit 10 is sufficiently stiff to avoid kinking during use.

Still referring to FIGS. 1 and 2, the vascular conduit 10 further comprises an interface portion 32 that comprises a sleeve 34 comprising a third synthetic material for permitting enhanced securement of the vascular conduit 10 to a patient during use. During use, particularly when the patient is ambulatory, there is a tendency for a transdermal conduit to move relative to the patient at the exit site. Having an anchoring device with a configuration and characteristic that permits a physician to suture the conduit to the patient would be a significant advantage. Preferably, the anchoring device comprises a sleeve 34 comprised of a third synthetic material having a textile property to enhance the use of sutures as a means for securing the catheter to the patient. More preferably, the sleeve 34 is made of polyester or other material having similar properties. The sleeve 34 is bonded to the conduit 10 in a manner to prevent relative movement between the sleeve and the catheter. The length of the sleeve 34 should be sufficient to give some flexibility to the physician in the placement of the cannula with respect to the exit site. In one embodiment, the sleeve 34 is manufactured already bonded to the catheter with a length pre-selected to give flexibility to the physician. If desired, the sleeve length may be kept at a minimum but be manufactured discretely from the conduit, permitting the physician to locate the sleeve where desired and then to bond the sleeve to the catheter after it is optimally positioned on the catheter. For short-term use, a technique as simple as clamping the extracorporeal portion of the sleeve to the catheter wall without occluding the inner flow path might be acceptable. For longer term use, bonding with an adhesive at the proximal end of the sleeve with a bonding material that would not travel undesirably toward the skin and into the patient would be desired.

Figure 3:
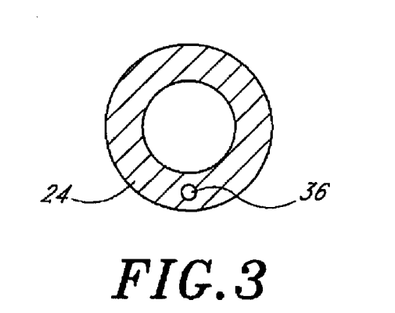
FIG. 3 is an axial cross-section view of the embodiment of FIG. 1 taken along section 3—3.
Figure 4:
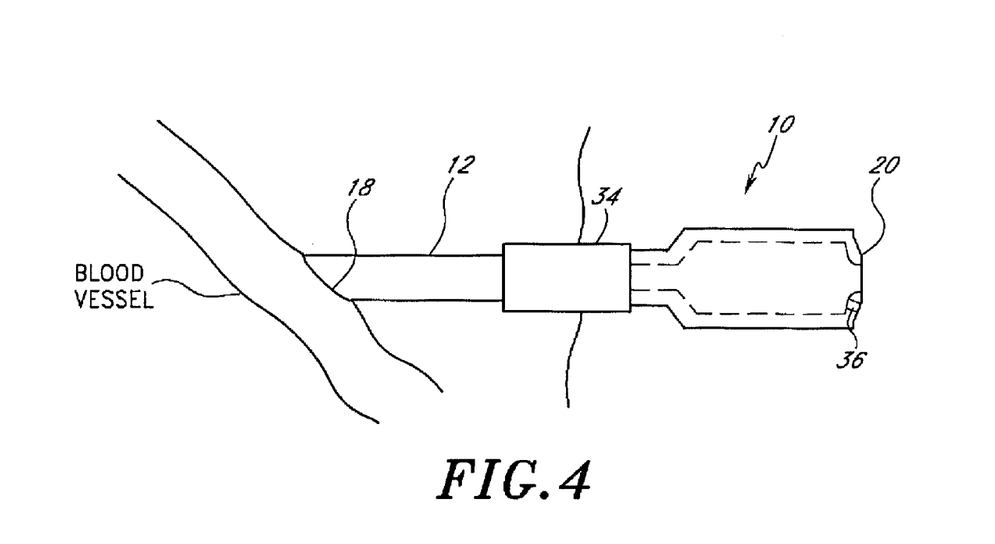
FIG. 4 is a schematic view showing application of the embodiment of FIG. 1 to a patient.

Referring to FIGS. 3 and 4, the conduit 10 may further comprise a small vent 36 in the vascular conduit 10 at the proximal end of the third portion 24 to vent air undesirably trapped in the conduit during use. The vent 36 is sufficiently large to permit air to pass through but sufficiently small to preclude the passage of blood.

Figure 5:
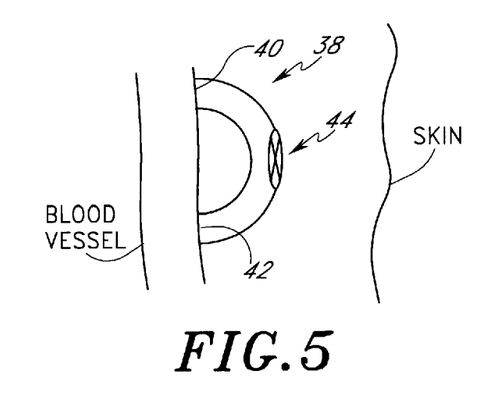
FIG. 5 is a schematic view showing application of another embodiment of the present invention to the patient.

As shown in FIG. 5, the present invention may further comprise a vascular shunt 38 having opposing ends 40, 42 that are configured to attach to a patient's vascular system. The vascular shunt ends 40, 42 may be secured to a blood vessel via, for example, an end-to-side anastomosis connection. Like the first and second portions 12, 14 of the conduit 10, the vascular shunt 38 comprises a first biocompatible material 16, such as PTFE, including ePTFE, or woven polyester. The vascular shunt provides an alternative path for blood flow, and as a result, the vascular shunt remains free from thrombi and blood can freely flow. The vascular shunt 38 comprises one or more access ports 44 for connecting the extracorporeal conduit 10. The access port 44 may be, for example, a self-sealing membrane or a bio-compatible valve. In this embodiment, therefore, the conduit can be repeatably connected and disconnected to the patients vascular system, via the shunt 38 through the access port(s) 44 without degrading the vessel wall strength. The advantage of this alternative embodiment is that a patient may be subject to periodic treatments (or periodic blood monitoring or drug infusion) without having to repeatably connect and disconnect to the patient's blood vessel. With this arrangement, the treating physician need only connect the vascular conduit 10 to the vascular shunt 38 and treat the patient as desired.

Figure 6:
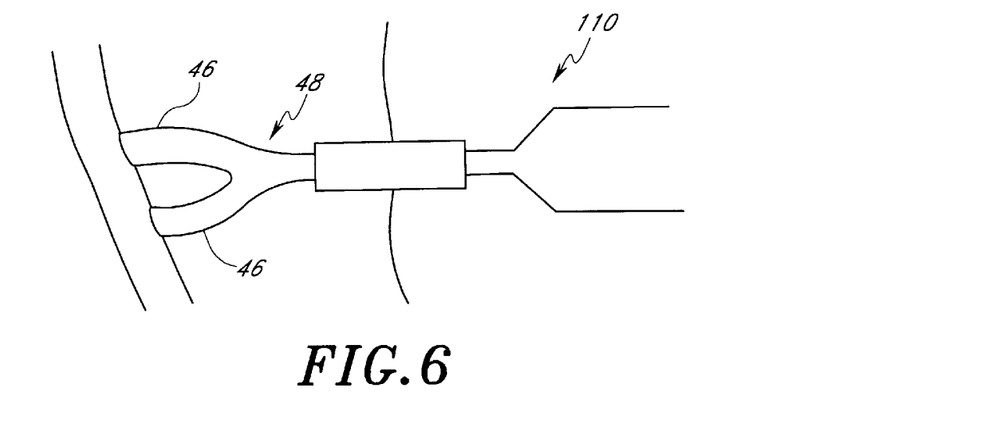
FIG. 6 is a schematic view showing yet another embodiment of the present invention with multiple connections to the same vessel.

As can be seen in FIG. 6, another embodiment of the present invention comprises a conduit 110 comprising a plurality of discrete smaller conduits 46, each of which may be connected to the patient's vascular system at different locations at the distal end 18 of the vascular conduit 10. By providing multiple connection conduits 46, smaller conduits can be used while maintaining a sufficient volume of blood flow. This addresses, among other things, sealing problems encountered when large conduits are connected to small vessels. The connection conduits 46 converge at a junction 48 proximal to the point of blood vessel penetration, but distal of the penetration site through the patient's body so that blood flows out of the body in one conduit. Each of the connection conduits 46 may be connected to a patient's vascular system via, for example, an end-to-side anastomosis connection.

Figure 7:
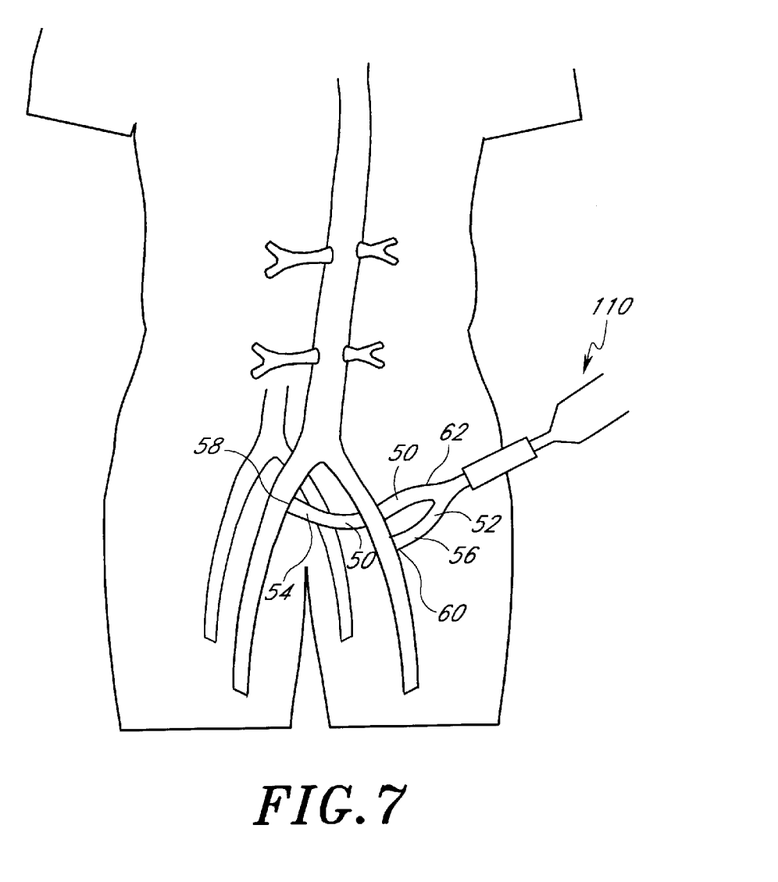
FIG. 7 is a schematic view showing another application of the embodiment illustrated in FIG. 6 with connection to multiple vessels of the patient's vascular system.

FIG. 7 shows another application of the embodiment illustrated in FIG. 6 wherein the vascular conduit 10 comprises a plurality of connection conduits 54, 56. The connection conduits 54, 56 are separated at their distal ends 58, 60 and each is configured to connect to different blood vessels within the patient's vascular system. The connection conduits 54, 56 converge at a junction 62, which is located within the first portion 12. Each of the distal ends 58, 60 may be connected to a patient's vascular system via, for example, an end-to-side anastomosis connection. In this way, blood may flow out of two different blood vessels in the patient's vascular system into the conduit 10. Of course, the conduit 10 can also be used to carry blood into two different blood vessels through the two lumens 50, 52.

Figure 8:
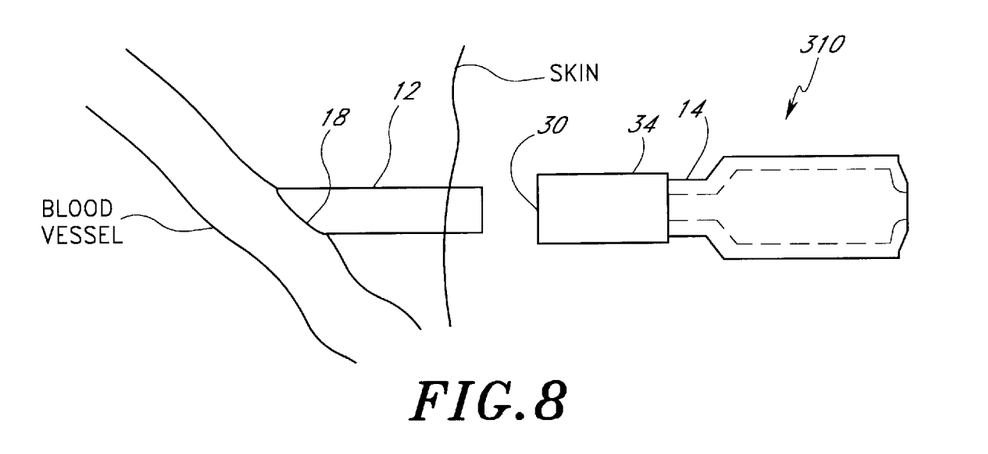
FIG. 8 is a schematic view showing yet another embodiment wherein the first portion may be disconnected from the rest of the vascular conduit.
Figure 9A:
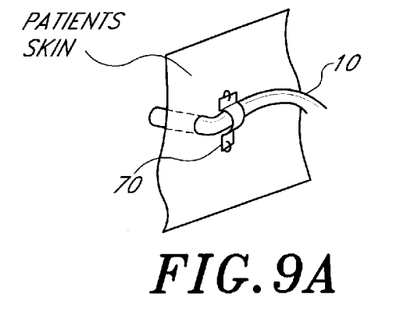
FIG. 9 illustrates some of the anchoring devices that can be used to immobilize the vascular conduit.
Figure 9B:
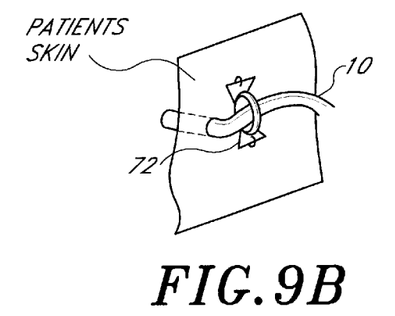
Figure 9C:
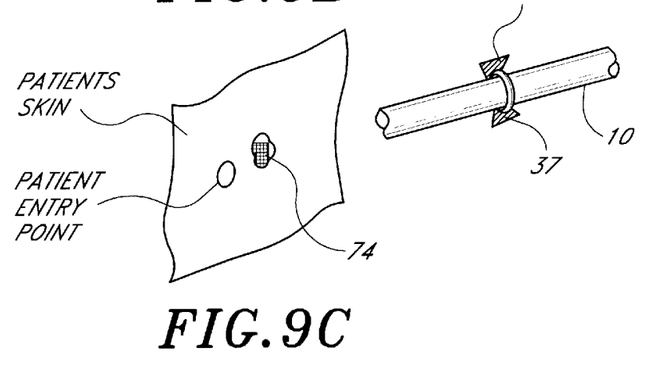
Figure 9D:
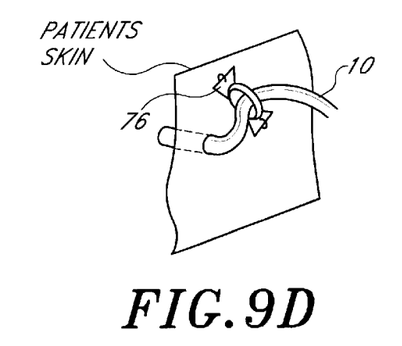

In an alternative embodiment shown in FIG. 8, the vascular conduit 10 may be configured so that the first portion 12 is made discrete from the second portion 14 so as to be repeatably disconnectable. In other words, it is contemplated that a mechanical connection be provided at the junction of the first and second portions to permit connection and disconnection thereof without adversely affecting fluid flow when connected or adversely affecting the patient when disconnected. Obviously, some means for abating blood flow would be necessary with such an alternative embodiment, such as a valve, preferably positioned just outside the patient's body. By doing so, the abatement means may be easily accessed when it is desired to connect or disconnect the first and second discrete portions during treatment. With application of the present inventive extracorporeal graft catheter, the abatement means may be a hemostat to clamp the proximal end of the first portion that protrudes a short distance outside the patient. With longer term and extended application, a more durable and safe valve may be employed. The advantage of this alternative embodiment is that a patient may be subject to periodic treatments (or periodic blood monitoring or drug infusion) without having to remove the distal portion of the extracorporeal graft from the patient's blood vessel. With this arrangement, the treating physician need only connect the second portion of the catheter to the abatement means at the proximal end of the first portion and treat the patient as desired.

Thrombosis is a common reaction when blood comes into contact with foreign matter inside or outside of the vasculature. This can interfere with treatments involving contact with foreign matter, such as the conduits herein described.

This problem is especially acute in longer term treatments where significant build-up can occur due to the length of time blood is flowing in the vascular conduits. As a result, certain coatings can be beneficial if applied to cannulae inserted into the vasculature. For example, an anti-thrombotic coating is especially useful for long-term treatments because it prevents adhesion of blood components to the coated surface, which might otherwise eventually block or severely restrict a lumen. For this reason, at least the interior of the first portion 12, the second portion 14 and the third portion 24 may have an anti-thrombotic coating. Also, if any other vascular conduit component is exposed to the interior lumen(s) of the vascular conduit 10, it too may have an anti-thrombotic coating, if desired.

Because patients using this vascular conduit preferably are ambulatory, there is an increased risk of infection at the patient's exit site. Consequently, anti-microbial or anti-bacterial coating may be beneficial, especially in long-term treatments. When placed at least on the exterior surface of the vascular conduit 10, this coating reduces the chance of infection occurring at or near the patient's exit site. Of course, any securing device used in connection with the vascular conduit 10, such as the sleeve 34, may also advantageously use an anti-microbial or anti-bacterial coating to reduce the risk of infection of the patient's exit site.

A preferred method of use of the present invention comprises the steps of (a) providing an extracorporeal vascular conduit comprising a first synthetic biocompatible material that extends substantially the length of the catheter, a second synthetic coating material employed over the portion of the catheter that extends outside the patient's body so as to form generally first and second portions of the catheter, and a third synthetic interface material to enhance securement of the catheter to the patient's skin, (b) securing a distal end of the extracorporeal vascular conduit to the patient's vascular system, and (c) connecting a proximal end of the extracorporeal vascular conduit to a pump, monitor, or other medical device used in and/or during the treatment of the patient. The present method could further include the steps of (d) providing a vascular shunt comprising a conduit made of synthetic biocompatible material, (e) securing a first end of the shunt and a second end of the vascular shunt to the patient's vascular system, and (f) securing a distal end of the extracorporeal vascular conduit to the vascular shunt when it is desired to effect treatment of the patient. Other variations in these two methods are contemplated that provide for the advantages described herein.

The present invention has, as one advantage, effectively permitting extended extracorporeal blood diversion during treatment of a patient. For example, the present invention could be used with the system and method for treating, inter alia, congestive heart failure that was developed by Orqis Medical, Inc., formerly Fore Flow Corporation. Details of such system and method are found in U.S. Ser. No. 09/166,055, now U.S. Pat. No. 6,273,909 to Bolling, and U.S. Ser. No. 09/289,231 to Bolling, Ser. No. 09/470,841 to Bolling et al., and Ser. No. 09/552,979 to Bolling et al., each of which are incorporated in their entirety by reference. The present invention could be particularly useful in enhancing the beneficial effects of such a system on the patient by minimizing the potential adverse effects of using synthetic materials for extracorporeal blood flow. The present invention could also be particularly useful where there is a desire to establish a single connection to the patient's vascular system for repeated monitoring of blood or for repeated infusion of drugs or other fluids over an extended period of treatment. Where it is desired to implement the system, as described in the above-identified patent applications incorporated by reference herein, in a manner where the pump is positioned external to the patient, a treating physician may connect the present extracorporeal vascular conduit 10 at both the inflow connection site and the outflow connection site; e.g., the left axillary artery and the left femoral artery, respectively.

In an alternative embodiment of the present extracorporeal vascular conduit, more than one lumen may be provided. In the embodiments described above, a single lumen was provided. Where it desired to have more than one path for fluid flow at a single site, a multi-lumen extracorporeal vascular conduit may be employed. Because it is contemplated that the present invention vascular conduit would be surgically connected to the patient's vasculature, the multi-lumen embodiment may be fashioned in at least one of two ways. In one version, a single housing having two lumens created therein may be provided, wherein the single housing is made of biocompatible material for substantially all of the first and second portions, with a protective coating provided on substantially all of the second portion intended to project outside the patient's body. The distal ends of the two lumens may then project outside the housing in a manner that would permit connection of each lumen separately to two positions on the same blood vessel or to two separate blood vessels. Likewise, the proximal ends of the two lumens would project outside the housing in a manner that would permit connection of each lumen to two separate medical devices or to an inflow and outlet end of a single pump. In an alternative version, the two lumens would be discrete but secured together so as to eliminate an integrating housing.

With regard to anchoring the present invention extracorporeal conduit to a patient, anchoring devices other than the sleeve 34 would be acceptable. For example, as shown is FIG. 9, a semi-circular bracket 70 having a inner diameter approximately equal to the outer diameter of the conduit near the skin exit and having tabs extending outwardly from the conduit near the skin could be used. The bracket should be dimensioned such that the semi-circular portion accepts a portion of the conduit, providing a friction fit with the conduit when the bracket is secured to the patient. The outwardly extending tabs could be connected to the skin to immobilize the conduit, preventing movement of the conduit with respect to the vessel to which it is attached. The outwardly extending tabs might be made with holes or some other feature to facilitate immobilization of the conduit via, for example, sutures.

Another suitable example of an anchoring mechanism would be a ring 72 having an inner perimeter approximately equal to the outer perimeter of the conduit near the skin exit. The ring would be slideable with respect to the conduit, but would provide sufficient friction fit to immobilize the conduit with respect to the vessel. As with the bracket, the ring would likely be made with some type of anchoring feature. This could include flanges extending outwardly from the ring on the side of the ring that lies between the patient and the conduit housing. These flanges could have suturing feature, such as holes or posts making securing of the anchoring device easier and less prone to break free from the skin.

Yet another example anchoring mechanism that could be used in conjunction with the ring or the semi-circular bracket described above would be a Velcro pad 74 with medical grade adhesive on the back side, which could be secured to the patient's skin. A mating Velcro portion could be affixed to the ring, bracket or other similar anchoring device, immobilizing the conduit with respect to the vessel to which it is attached.

Another anchoring device would be a cloth loop 76 which could be wrapped around the conduit near the patient's exit site. This loop could be pulled sufficiently tight to provide a snug fit around the conduit. The ends of the cloth could be used to suture the conduit to the patient to immobilize the conduit and prevent relative motion between the conduit and the patient's vessels. Also, suturing features could be attached to the ends of the cloth strip to facilitate securement of the cloth loop anchoring device to the patient. As discussed above, the Velcro approach could also be used with the cloth loop to immobilize the conduit.

Suitable materials for the anchoring devices include silicones, polymers (for example, polyethylene and polyurethane), rubber and others known to those skilled in the art. Of course, these materials and anchoring devices are merely examples of the numerous different structures that can be used to immobilize the conduit to prevent relative motion between the conduit and the patients vessel.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An extracorporeal vascular conduit comprising at least in part a first synthetic biocompatible material, said vascular conduit having a first portion with a first distal end configured to be attached to at least one blood vessel of a patient, said first portion comprising said biocompatible material and configured to compatibly reside within the patient's body for an extended period of time without adverse effects to said patient, said vascular conduit having a second portion also comprising said biocompatible material and being configured so as to reside outside the patient's body for extended periods of time without significantly adversely affecting the patient, said second portion having a proximal end configured to connect to an external component employed in the treatment of said patient, the vascular conduit further comprising a second synthetic material that covers a substantial portion of said second portion of said vascular conduit, said synthetic material providing a substantially impervious and nonporous barrier between the ambient environment and any fluid flowing: within the interior of the vascular conduit when said vascular conduit is in use.

2. The vascular conduit of claim 1 wherein the first biocompatible material is PTFE.

3. The vascular conduit of claim 1 wherein the second synthetic material is a polymer.

4. The vascular conduit of claim 1 further comprising a sleeve comprising a third synthetic biocompatible material having a generally textile characteristic, said sleeve positioned on said conduit so that when said conduit is applied to a patient, the sleeve is positioned at and surrounding the interface of the first and second portions of said vascular conduit, said sleeve serving to provide a substrate upon which a treating physician may secure said vascular conduit to the patient to minimize relative movement therebetween.

5. The vascular conduit of claim 1 further comprising an anchoring device.

6. The vascular conduit of claim 4 wherein the third material is polyester.

7. An extracorporeal vascular conduit comprising a first portion comprising a first synthetic biocompatible material, a second portion comprising said biocompatible material and a second synthetic non-porous coating material, and a third portion enveloping some of the first and second portions and comprising a third synthetic material, said first portion having a distal end configured to be secured to a blood vessel of a patient and having a proximal end configured to be connected to an external component used during treatment of the patient.

8. A method of circulating fluid outside a patient's body comprising the steps of:

providing an extracorporeal vascular conduit comprising a first and second portion, said first and second portion comprising a first synthetic biocompatible material, said second portion further comprising a second synthetic coating material;

attaching a distal end of the vascular conduit to a first blood vessel location; and connecting a proximal end of the vascular conduit to an extracorporeal device used in the treatment of the patient.

9. The method of claim 8 wherein said first synthetic biocompatible material is ePTFE.

10. The method of claim 8 wherein said second synthetic material is silicone.

11. The extracorporeal vascular conduit of claim 1 wherein the distal end further comprises at least one additional connection conduit configured to be attached to a blood vessel.

12. An extracorporeal conduit system comprising a vascular shunt and a vascular conduit said vascular shunt comprising a first synthetic biocompatible material, said vascular shunt having a first end and a second end configured to be attached to a blood vessel of a patient, said vascular conduit comprising said biocompatible material, said vascular conduit having a first portion with a first distal end configured to be attached to said vascular shunt, said shunt and said first portion configured to compatibly reside within the patient's body for an extended period of time without adverse effects to said patient, said vascular conduit having a second portion also comprising the first biocompatible material, said second portion being configured so as to reside outside the body for extended periods of time without significantly adversely affecting the patient.

13. The vascular shunt of claim 12 further comprising an access port.

14. The vascular shunt of claim 12 wherein said biocompatible material is ePTFE.

* * * * *